US010551378B2

(12) United States Patent
Gouda et al.

(10) Patent No.: US 10,551,378 B2
(45) Date of Patent: Feb. 4, 2020

(54) TISSUE STAINING METHOD

(75) Inventors: Hideki Gouda, Tokyo (JP); Hisatake Okada, Tokyo (JP); Yasushi Nakano, Tokyo (JP); Kohsuke Gonda, Sendai (JP); Noriaki Ohuchi, Sendai (JP); Mika Watanabe, Sendai (JP)

(73) Assignee: KONICA MINOLTA, INC., Tokyo (JP)

(*) Notice: Subject to any disclaimer, the term of this patent is extended or adjusted under 35 U.S.C. 154(b) by 0 days.

(21) Appl. No.: 14/342,829

(22) PCT Filed: Sep. 4, 2012

(86) PCT No.: PCT/JP2012/072445
§ 371 (c)(1),
(2), (4) Date: Mar. 5, 2014

(87) PCT Pub. No.: WO2013/035688
PCT Pub. Date: Mar. 14, 2013

(65) Prior Publication Data
US 2014/0212889 A1 Jul. 31, 2014

(30) Foreign Application Priority Data
Sep. 9, 2011 (JP) ................................. 2011-197338

(51) Int. Cl.
G01N 33/569 (2006.01)
(52) U.S. Cl.
CPC ................................. G01N 33/569 (2013.01)
(58) Field of Classification Search
CPC ...................................................... G01N 33/569
See application file for complete search history.

(56) References Cited

U.S. PATENT DOCUMENTS

| 4,326,008 | A  |   | 4/1982  | Rembaum |
| 4,934,811 | A  | * | 6/1990  | Watts ................. G01N 21/8507 250/227.11 |
| 5,326,692 | A  |   | 7/1994  | Brinkley et al. |
| 6,114,038 | A  | * | 9/2000  | Castro ..................... B82Y 5/00 257/614 |
| 6,642,062 | B2 | * | 11/2003 | Kauvar ............. G01N 33/54313 435/6.1 |
| 6,790,636 | B1 | * | 9/2004  | Star et al. ..................... 435/40.5 |
| 6,893,837 | B2 | * | 5/2005  | Slamon et al. ............... 435/40.5 |
| 7,892,748 | B2 | * | 2/2011  | Norrild et al. ................. 435/7.1 |
| 8,111,897 | B2 |   | 2/2012  | Yamashita et al. |
| 8,131,476 | B2 |   | 3/2012  | Cline et al. |
| 2003/0073149 | A1 | * | 4/2003  | Archer ..................... B82Y 5/00 435/7.92 |
| 2003/0148544 | A1 | * | 8/2003  | Nie et al. ........................ 436/524 |
| 2004/0116409 | A1 |   | 6/2004  | Campochiaro |
| 2005/0032132 | A1 |   | 2/2005  | Niki et al. |
| 2006/0177451 | A1 |   | 8/2006  | van den Oudenrijn et al. |
| 2006/0193830 | A1 |   | 8/2006  | Hauswirth et al. |
| 2008/0032328 | A1 | * | 2/2008  | Cline et al. ................... 435/40.5 |
| 2009/0297500 | A1 |   | 12/2009 | Nakamura et al. |
| 2011/0182490 | A1 | * | 7/2011  | Hoyt .................. G06K 9/00147 382/128 |
| 2012/0112098 | A1 | * | 5/2012  | Hoyt ...................... B82Y 30/00 250/459.1 |
| 2012/0292572 | A1 | * | 11/2012 | Yang ...................... C01B 33/18 252/301.35 |

FOREIGN PATENT DOCUMENTS

| JP | 2007-285918 | 11/2007 | |
| JP | 2008-510126 | 4/2008 | |
| JP | 2009-115599 | 5/2009 | |
| JP | 2010-500571 | 1/2010 | |
| JP | 2011-149826 | 8/2011 | |
| WO | 03010542 A1 | 2/2003 | |
| WO | 03080648 A2 | 10/2003 | |
| WO | 2005000694 A2 | 1/2005 | |
| WO | 2009/116266 | 9/2009 | |
| WO | WO 2011042564 A1 * | 4/2011 | ....... G01N 33/54346 |
| WO | WO-2011088627 A1 * | 7/2011 | ............. C01B 33/18 |

OTHER PUBLICATIONS

Panchuk-Voloshina et al., Alexa Dyes, a Series of New Fluorescent Dyes that Yield Exceptionally Bright, Photostable Conjugates, The Journal of Histochemistry and Cytochemistry, 47(9):1179-1188, 1999.*
UCSD, Mouse Phenotyping, 2 page, 2008, retrieved from http://web.archive.org/web/20080319013005/http://mousepheno.ucsd.edu/hematoxylin.shtml on Aug. 3, 2015.*
Scientific, Sulfohodamine 101, 4 pages, retrieved from https://www.thermofisher.com/order/catalog/product/5359 on Sep. 24, 2017 (Year: 2017).*
Extended European Search Report dated Feb. 6, 2015 for corresponding Patent Application No. 12829474.1.
New Journal of Chemistry 33, p. 561 (2009) (8 pages).
Nature Biotechnology 19, p. 631 (2001) (6 pages).
International Search Report, PCT/JP2012/072445 (4 pages).
Notification of Reason for Refusal dated Oct. 11, 2016 from corresponding Japanese Application; Patent Application No. 2013-532597; English translation of Notification of Reason for Refusal; Total of 6 pages.

* cited by examiner

*Primary Examiner* — Andrea S Grossman
(74) *Attorney, Agent, or Firm* — Lucas & Mercanti, LLP

(57) ABSTRACT

It is an object of the present invention to provide a tissue staining method that makes it possible to observe both information on the morphology of a tissue and information on a biological substance such as an antigen molecule to be detected on a single section and in a single view field. The present invention provides a tissue staining method, including carrying out (A) a HE (hematoxylin-eosin) staining, and (B) a histochemical staining, serially on a single tissue section, wherein the histochemical staining is defined as a histochemical technique for detecting a biological substance to be detected in a tissue in a visible manner by use of a binding reaction between the biological substance to be detected and a probe biological substance capable of binding specifically to the biological substance to be detected.

7 Claims, No Drawings

TISSUE STAINING METHOD

CROSS REFERENCE TO RELATED APPLICATION

This Application is a 371 of PCT/JP2012/072445 filed on Sep. 4, 2012 which, in turn, claimed the priority of Japanese Patent Application No. JP2011-197338 filed on Sep. 9, 2011 both applications are incorporated herein by reference.

TECHNICAL FIELD

The present invention relates to a tissue staining method.

BACKGROUND ART

HE (hematoxylin-eosin) stain uses hematoxylin and eosin as a dye, and is widely used in the field of histology for observing tissue sections. Among them, hematoxylin is a blue-violet dye, and has a property of staining basophilic tissues such as cell nuclei, bone tissues, part of cartilage tissues, and serous components. Eosin, on the other hand, is a red to pink dye, and has a property of staining eosinophilic tissues such as cytoplasm, connective tissues of the soft tissue, red blood cells, fibrin, and endocrine granules. Due to such properties of hematoxylin and eosin, HE stain is widely used to obtain morphological information on tissue specimens.

On the other hand, immunohistochemistry (IHC) is widely known as a histological (histochemical) tool for detecting an antigen in a tissue specimen using an antibody. The immunohistochemistry may be referred to as "immunological staining" due to the process of color development for visualizing an antigen-antibody reaction which is otherwise invisible (hereinafter, the term "immunohistochemical staining" may be used for immunohistochemistry). Due to the characteristics of visualizing the location of an antigen-antibody reaction, immunohistochemistry is widely used in the fields of medicine and life chemistry for the purpose of detecting a location of a biological substance in a tissue specimen.

As a histological (histochemical) technique related to immunohistochemistry, lectin staining is also known. The lectin staining is a technique that utilizes a property of lectin of binding to a specific sugar chain in a non-immunological and specific manner in order to detect a sugar chain in a tissue specimen using lectin, and is widely used in fields related to sugar chains.

All of the HE staining, immunohistochemistry and lectin staining are used as methods for detecting a location of cancer cells in a cell specimen. For example, when it is desired to confirm a location of cancer cells in a cell specimen, a pathologist, in order to determine the presence or absence of cancer cells in the cell specimen, conventionally prepared a plurality of tissue sections (hereinafter referred to as "sections") from a tissue specimen; subjected a first section to HE staining in order to obtain its morphological information, and determined the presence or absence of cancer cells; and prepared, by use of a second section, a dye-deposited section by an enzymatic reaction and determined the presence or absence of target molecules. While there were cases where, instead of immunohistochemistry, lectin staining was used in conjunction with HE staining, similar procedures were used therein. For diseases other than cancer as well, similar procedures were generally used in detecting the focus of a disease in a cell sample with HE staining and immunohistochemistry (or lectin staining). The observation of an identical site with two sections requires a lot of work and expertise, which caused a source for variation in pathological diagnosis. Under such circumstances, methods have been tested that attempt to determine the presence or absence of a target molecule by binding a fluorescent body such as a fluorescent dye or semiconductor nanoparticles (quantum dots) to antibody. However, these methods have problems that such a fluorescent body can only emit a small amount of fluorescence. Thus, proper separation and removal of autofluorescence resulting from the section per se were prerequisite in order to determine a location of the target molecule based on fluorescence from the fluorescent body, and in addition the HE staining of another section was still necessary to obtain morphological information.

SUMMARY OF THE INVENTION

Problems to be Solved by the Invention

It is an object of the present invention to provide a tissue staining method that makes it possible to observe both information on the morphology of a tissue and information on a biological substance such as an antigen molecule to be detected on a single section and in a single view field.

Means to Solve the Problems

After intensive and extensive research to attain the object of the present invention, the present inventors have found that by carrying out a histochemical staining such as an immunohistochemical staining using a specific binding reaction between biological substances in conjunction with a HE (hematoxylin-eosin) staining on a single tissue section, information on the presence or absence of a target molecule in the tissue section can be obtained, and information on the location of the target molecule can also be obtained through the simultaneously obtained morphological information of the tissue, and thereby have completed the present invention.

Thus, the present invention provides a tissue staining method represented by the following [1] through [10]:

[1] A tissue staining method, comprising carrying out
  (A) a HE (hematoxylin-eosin) staining, and
  (B) a histochemical staining,
serially on a single tissue section, wherein the histochemical staining is defined as a histochemical technique for detecting a biological substance to be detected in a tissue in a visible manner by use of a binding reaction between the biological substance to be detected and a probe biological substance capable of binding specifically to the biological substance to be detected.

[2] The tissue staining method according to the above [1], wherein said histochemical staining (B) is carried out first, and then said HE staining (A) is carried out.

[3] The tissue staining method according to the above [2], wherein a fixation treatment is carried out after said histochemical staining (B) is carried out and before said HE staining (A) is carried.

[4] The tissue staining method according to any one of the above [1] to [3], wherein a label used in said histochemical staining (B) is a substance that is chromogenic per se.

[5] The tissue staining method according to the above [4], wherein said substance that is chromogenic per se is a fluorescent body.

[6] The tissue staining method according to the above [5], wherein said fluorescent body is a fluorescent aggregate comprising a plurality of aggregated fluorescent substances.

[7] The tissue staining method according to the above [5] or [6], wherein the emission wavelength of said fluorescent body is 580 nm or greater.

[8] The tissue staining method according to any one of the above [5] to [7], wherein the excitation wavelength of said fluorescent body is 350 nm or greater and 400 nm or less, or 560 nm or greater and 630 nm or less.

[9] The tissue staining method according to any one of the above [1] to [8], wherein said histochemical staining (B) is immunohistochemical staining.

[10] The tissue staining method according to any one of the above [1] to [8], wherein said histochemical staining (B) is lectin staining.

Effects of the Invention

According to the present invention, by carrying out a histochemical staining using a specific binding reaction between biological substances, such as an immunohistochemical staining, in conjunction with a HE (hematoxylin-eosin) staining on a single tissue section, it becomes possible to observe a morphological image of cells etc. together with a histologically stained image reflecting the distribution of a target biological substance such as an antigen molecule on a single section and in a single fluorescent view field, and thus it can enhance diagnostic precision by the pathologist and can increase convenience.

MODES FOR CARRYING OUT THE INVENTION

Hereinbelow, modes for carrying out the present invention will be explained, but the present invention is not limited to them. Hereinbelow, the present invention and the constituent elements thereof and the best modes for carrying out the present invention will be explained in detail.

[Component Material]
Label

As used herein, a label is used to visualize a biological substance to be detected that is present on a tissue section, when the section is subjected to a histochemical staining (B) described below. While a label used in the present invention is not specifically limited as long as it does not inhibit a binding reaction between a biological substance to be detected and a probe biological substance capable of binding specifically to the biological substance to be detected (hereinafter referred to as a "specific binding reaction between biological substances"), such as an antigen-antibody reaction, or does not inhibit quantitative performance in measurement, a label is preferably used which can detect via color development the presence of a complex formed by a specific binding reaction between biological substances, because they can directly visualize the specific binding reaction between biological substances, specifically in a directly visible manner to the naked eye. As used herein the term "to visualize in a directly visible manner" means that a direct observation of a location of a specific binding reaction between biological substances can be attained without any secondary procedures such as image development. Such a label includes a substance that is chromogenic per se.

<A Substance that is Chromogenic Per Se>

The "substance that is chromogenic per se" as a label for use in the present invention is not specifically limited as long as it can easily identify the presence or absence of a complex formed from a specific binding reaction between biological substances. However, from the viewpoint of ease in identifying color development, a light-emitting substance such as a fluorescent body may preferably be used as the "substance that is chromogenic per se."

As used herein a light-emitting substance refers to a substance that emits light during the process of being excited by external energy and returning to the ground state from the excited state, that is, a substance that emits light by luminescence. The "external energy" as used herein includes an electromagnetic wave, heat, friction, chemical reaction, and the like. Also, the embodiments of light emission include light emission associated with inactivation from the excited singlet state and light emission associated with inactivation from the triplet state.

As the light-emitting substance of the present invention, a fluorescent body may preferably be used. As used herein "fluorescent body" generally refers to a substance that emits light during the process of being excited by irradiation with an external X-ray, ultraviolet ray, or visible light and returning to the ground state from the excited state. Thus the "fluorescent body" as used herein is not concerned with the transition mode of returning to the ground state from the excited state, and may be a substance that emits fluorescence in a narrow sense, that is, light emission associated with inactivation from the excited singlet state or substances that emits phosphorescence that is light emission associated with inactivation from the triplet state. The "fluorescent body" as used herein is not limited by the life span of light emission after blocking the excitation light. Thus, the fluorescent body may be a substance that is known as a light-storing substance such as zinc sulfate and strontium aluminate.

The fluorescent bodies as used herein include fluorescent substances such as an organic fluorescent dye and semiconductor nanoparticles, and fluorescent labels such as a fluorescent aggregate including a plurality of aggregated fluorescent substances.

The organic fluorescent dyes include a fluorescein-based dye molecule, a rhodamine-based dye molecule, an Alexa Fluor (manufactured by Invitrogen)-based dye molecule, a BODIPY (manufactured by Invitrogen)-based dye molecule, a cascade-based dye molecule, a coumarin-based dye molecule, a NBD-based dye molecule, a pyrene-based dye molecule, a Texas Red-based dye molecule, a cyanine dye molecule, a perylene-based dye molecule, an oxazine-based dye molecule, and the like.

Specifically, the organic fluorescent dyes can include 5-carboxy-fluorescein, 6-carboxy-fluorescein, 5,6-dicarboxy-fluorescein, 6-carboxy-2',4,4',5',7,7'-hexachloro fluorescein, 6-carboxy-2',4,7,7'-tetrachloro fluorescein, 6-carboxy-4',5'-dichloro-2',7'-dimethoxy fluorescein, fluorescein-5-isocyanate (FITC), naphthofluorescein, 5-carboxy-rhodamine, 6-carboxy-rhodamine, 5,6-dicarboxy-rhodamine, rhodamine 6G, tetramethyl rhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (all of the above being manufactured by Invitrogen), methoxy coumarin, NBD, pyrene, Texas Red, Cy5, Cy5.5, Cy7, and the like. They may be used singly or in mixtures of a plurality of them.

These organic fluorescent dyes may be used singly or in combination of two or more of them.

As the semiconductor nanoparticles, any of semiconductor nanoparticles including, as their component, group II-VI compounds, group III-V compounds, group I-III-VI compounds, and group IV elements ("Group II-VI semiconductor nanoparticles", "Group III-V semiconductor nanoparticles", "Group I-III-VI semiconductor nanoparticles", and "group IV semiconductor nanoparticles," respectively) can be used. The use of semiconductor nanoparticles as the fluorescent substance in the present invention may be preferred, since that enables to observe a location of a biological substance to be detected in the form of bright spots.

Specifically, there can be mentioned, but not limited to, CdSe, CdS, CdTe, ZnSe, ZnS, ZnTe, InP, InN, InAs, InGaP, GaP, GaAs, CuInS, CuInSe, AgInSe, AgInS, CuInGaS, Si, and Ge.

These semiconductor nanoparticles may be used singly or in combination of two or more of them.

According to the present invention, there can be used semiconductor nanoparticles which have a core/shell structure in which the above semiconductor nanoparticles are used as the core with a shell being provided thereon. As a method of notating semiconductor nanoparticles having a core/shell structure in the present description, when the core is CdSe and the shell is ZnS, it is notated as CdSe/ZnS. For example, there can be used, but not limited to, CdSe/ZnS, CdS/ZnS, InP/ZnS, InGaP/ZnS, Si/SiO$_2$, Si/ZnS, Ge/GeO$_2$, Ge/ZnS, and the like.

Semiconductor nanoparticles may be used whose surfaces have been treated with an organic polymer etc., as needed. Examples of them include CdSe/ZnS (manufactured by Invitrogen) having surface carboxy groups, CdSe/ZnS (manufactured by Invitrogen) having surface amino groups, and the like.

Other fluorescent substances that can be used in the present invention include rare earth fluorescent bodies, and the like. As rare earth fluorescent bodies, there can be mentioned neodymium oxide, neodymium chloride, neodymium nitrate, ytterbium oxide, ytterbium chloride, ytterbium nitrate, lanthanum oxide, lanthanum chloride, lanthanum nitrate, yttrium oxide, yttrium chloride, yttrium nitrate, praseodymium chloride, erbium chloride, and the like. Orthophosphate, ammonium phosphate and ammonium dihydrogen phosphate can be used.

Furthermore, according to the present invention, in addition to the above fluorescent substances, a fluorescent aggregate including a plurality of aggregated fluorescent substances can be used as a fluorescent body. Staining of tissue sections using as a fluorescent body a fluorescent aggregate including a plurality of aggregated fluorescent substances may be preferred, since it makes it possible to observe a location of a biological substance to be detected in the form of a bright spot even with a common microscope. As used herein the "fluorescent aggregate including a plurality of aggregated fluorescent substances" refers to an aggregate having aggregated fluorescent substances such as the above-mentioned organic fluorescent dyes and the above-mentioned semiconductor nanoparticles on the surface or inside thereof. Thus, the "fluorescent aggregate including a plurality of aggregated fluorescent substances" may be a fluorescent aggregate of a core/shell structure having a core capable of immobilizing a multitude of fluorescent substances and a plurality of fluorescent substances immobilized on the core, or a fluorescent aggregate in the form of fluorescent body-encapsulating nanoparticles of a structure having encapsulated a plurality of fluorescent substances in the substrate. As used herein the term "nanoparticle" is used to mean a particle having a dimension of a nanometer order (1 to several hundred nanometers).

Materials constituting the fluorescent aggregate include, but not limited to, polystyrene, polylactic acid, silica and the like.

The fluorescent aggregate can be prepared by a known method. For example, silica nanoparticles having fluorescent organic dyes aggregated therein can be synthesized by referring to the synthesis of FITC-encapsulating silica particles described in Langmuir 8, 2921 (1992). By replacing FITC with a desired fluorescent organic dye, a variety of silica nanoparticles having fluorescent organic dyes aggregated therein can be synthesized.

Silica nanoparticles having quantum dots aggregated therein can be synthesized by referring to the synthesis of CdTe-aggregated silica nanoparticles described in New Journal of Chemistry 33, 561 (2009).

Polystyrene nanoparticles having fluorescent organic dyes aggregated therein can be synthesized by referring to the copolymerization method using organic dyes having polymerizable functional groups described in U.S. Pat. No. 4,326,008 (1982) or the method of impregnating fluorescent organic dyes into polystyrene nanoparticles described U.S. Pat. No. 5,326,692 (1992).

Silica nanoparticles having quantum dots aggregated therein can be synthesized by referring to the method of impregnating quantum dots into polystyrene nanoparticles described in Nature Biotechnology 19, 631 (2001).

The average particle size of the fluorescent aggregate may be, but not limited to, generally about 30 to 800 nm, preferably 50 to 200 nm. The coefficient of variation that indicates variation in particle size may be, but not limited to, generally 20% or less, preferably 15% or less, and more preferably 5 to 15%. The average particle size as used herein is an arithmetic average obtained as a particle size which is a diameter of a circle in which electron micrographs are taken using a scanning electron microscope (SEM) and the cross-sectional area is measured for a sufficient number (1000, for example) of fluorescent substance nanoparticles and then the measured value is considered as the area of the corresponding circle, and the coefficient of variation is a value (100×standard deviation of particle size/average particle size) calculated from the particle size distribution measured as above. Thus, as used herein "average particle size" refers to a volume-average particle size.

Among the labels mentioned above, fluorescent bodies are preferably used, since they provide assured color development corresponding to the amount of a complex formed from the specific binding reaction between biological substances such as an antigen-antibody reaction. And, among the fluorescent bodies, fluorescent aggregates including a plurality of aggregated fluorescent substances may most preferably be used, since they provide high intensity of light emission and excellent quantitative performance.

Biological Substance to be Detected

A biological substance to be detected by the tissue staining method of the present invention (hereinafter referred to as the "biological substances to be detected") is, but not limited to, a substance that also functions as a target biological substance to which a probe biological substance described below specifically binds, since visualization with the above label can be performed via a specific binding reaction between biological substances such as an antigen-antibody reaction. In the tissue staining method of the present invention, since immunohistochemical staining may preferably be used as a tissue chemical staining (B)

described below, typical examples of the "biological substance to be detected" include a biological substance that functions as an antigen to an antibody.

As used herein the term "antigen" refers to a biological substance, specifically a molecule or molecule fragment. Such "molecules" or "molecule fragments" may include, for example, nucleic acid (single stranded or double stranded DNAs, RNAs, polynucleotides, oligonucleotides, PNAs (peptide nucleic acids) etc., or nucleoside, nucleotide, and modified molecules thereof), protein (polypeptides, oligopeptides etc.), amino acid (including modified amino acids), saccharide (oligosaccharides, polysaccharides, sugar chains etc.), lipid, or a modified molecule and a complex thereof, and may specifically be, but not limited to, a tumor marker, a signaling substance, a hormone etc. For example, when an antibody drug which is used as an anti-cancer agent is used as antibody, preferred target antigens include growth regulators, metastasis regulators, growth regulator receptors, and metastasis regulator receptors etc. of cancer.

Among such growth regulators, metastasis regulators, growth regulator receptors, and metastasis regulator receptors, examples of growth regulators of cancer and receptors thereof include cell growth factors and receptors thereof such as epidermal growth factor (EGF), EGF receptor (EGFR), platelet-derived growth factor (PDGF), PDGF receptor (PDGFR), insulin-like growth factor (IGF), IGF receptor (IGFR), fibroblast growth factor (FGF), FGF receptor (FGFR), vascular endothelial growth factor (VEGF), VEGF receptor (VEGFR), hepatocyte growth factor (HGF), HGF receptor (HGFR), neurotrophin (NT), transforming growth factor β (TGFβ) family, and HER2, and cell cycle regulating factors such as cyclin (cyclin), cyclin-dependent kinase (CDK: Cyclin-Dependent Kinase), cyclin A, cyclin B, cyclin D, cyclin E, CDK1, CDK2, CDK4, CDK6, p16INK, p15, p21, p27, RB (Retinoblastoma), etc. Also examples of metastasis regulators of cancer and receptors thereof include matrix metalloproteinase 1 (MMP1), matrix metalloproteinase 2 (MMP2), PAR1 (Protease Activated Receptor 1), CXCR4 (Chemokine [C-X-C motif] receptor 4), and CCR7 (Chemokine [C-C motif] receptor 7) etc., and among them, preferable examples may include HER2 since trastuzumab targeting HER2 is widely used.

In addition to antigen related to cancer, inflammatory cytokines such as TNF-α (tumor necrosis factor α), IL-6 (interleukin 6) receptor and virus-elated molecules such as RSV F protein can be targets to be detected by the staining method of the present invention.

On the other hand, when methods other than the immunohistochemical staining is used as the histochemical staining (B) described below in the tissue staining method of the present invention, the "biological substance to be detected" need not be a substance that functions as an antigen. For example, when lectin staining is used as the histochemical staining (B) described below, the "biological substances to be detected" include saccharides (oligosaccharides, polysaccharides, sugar chains etc.), or a modified molecules and complexes thereof, and they may be a tumor marker, a signaling substance, a hormone and the like.

Probe Biological Substance

As a medium for incorporating the above label into the "biological substance to be detected" present on a tissue section when the histochemical staining (B) described below is carried out according to the tissue staining method of the present invention, a probe biological substance that specifically binds to said "biological substance to be detected" (hereinafter referred to as "probe biological substance") is used. The "Probe biological substances" to be used in the tissue staining method of the present invention include antibody and lectin.

As used herein the term "antibody" is used in the meaning of including any antibody fragment or derivative, and may include various antibodies such as Fab, Fab'$_2$, CDR, humanized antibody, multifunctional antibody, and single chain antibody (ScFv).

In accordance with the present invention, for example, antibody which is a constituent of antibody drugs can be used for the immunohistochemical staining of tissue sections. As an antibody drug herein, one that is generally used in the treatment of autoimmune diseases such as rheumatoid arthritis, malignant tumors such as cancer, virus infections and the like may be used.

Representative antibody drugs that are in clinical use are shown in the following Table 1. For reference, in Table 1, antibody drugs that are used in the treatment of autoimmune diseases and infections are also described.

TABLE 1

Representative Antibody Drugs

| Target disease | Common name | Trade name | Target molecule |
|---|---|---|---|
| Cancer and related diseases | Rituximab | Rituxan: Registered trademark | CD20 |
| | Gemutuzumab | Mylotarg: Registered trademark | CD33 |
| | Alemtuzumab | Campath: Registered trademark | CD52 |
| | Ibritumomab | Zevalin: Registered trademark | CD20 |
| | Tositumomab | Bexxar: Registered trademark | CD20 |
| | Trastuzumab | Herceptin: Registered trademark | HER2 |
| | Bevacizumab | Avastin: Registered trademark | VEGF |
| | Cetuximab | Erbitux: Registered trademark | EGF receptor |
| | Panitumumab | Vectibix: Registered trademark | EGF receptor |
| Autoimmune diseases | Infliximab | Remicade: Registered trademark | TNF-α |
| Infections | Palivizumab | Synagis: Registered trademark | RSV F protein |

In the above Table 1, for example, "Herceptin" is an antibody drug and "trastuzumab" is an antibody (i.e. antibody drug-constituting antibody) contained as a constituent.

Among the antibody drugs shown in the above Table 1, gemutuzumab is used in the form of gemutuzumab-ozogamicin formed by binding to calicheamicin, an antitumor active substance.

Among the antibody drugs shown in the above Table 1, an antibody drug including trastuzumab as a constituent (i.e., Herceptin (registered trademark)) may preferably be used.

In addition, cancers to be subject to the staining method of the present invention can include colon cancer, rectal cancer, renal cancer, breast cancer, prostate cancer, uterine cancer, ovarian cancer, endometrial cancer, esophageal cancer, blood cancer, liver cancer, pancreatic cancer, skin cancer, lung cancer, and the like.

As used herein the term "lectin" is used as a generic term for proteins that specifically bind to sugar chains. Examples of lectin include "R-type lectin" found in all the living world including bacteria and related to ricin B chain, "calnexin/calreticulin" found in the entire eucaryotes and involved in the folding of sugar protein, a calcium auxotroph "C-type lectin" that is widely present in multicellular animals and includes representative lectins such as "selectin" and "collectin," "galectin" that is widely distributed in the animal world and shows specificity for galactose, "legume lectin" that forms a large family in the Leguminosae of plants, "L-type lectin" that has a structural similarity with this and is involved in the intracellular transport of animal cells, mannose 6-phosphate-binding "P-type lectin" that is involved in the intracellular transport of lysosomal enzymes, "annexin" that binds to acid sugar chains including glycosaminoglycan, "I-type lectin" that belongs to the immunoglobulin superfamily and includes "Siglec", and the like.

Representative lectins are shown in the following Table 2.

TABLE 2

Representative Lectins

| Lectin | | | Specificity |
| --- | --- | --- | --- |
| Abbreviation | Common name | Source | Sugar chain |
| Con A | concanavalin A | Jack-bean | Manα1→6(Manα1→3)Man |
| PNA | Peanut lectin | Peanut | Galβ1→3GalNAc |
| SBA | Soy bean lectin | Soy bean | GalNAcα1→3Gal |
| UEA-I | Furze lectin | Furze | Fucα1→2Galβ1→4GlcNAc |

Labeled Probe Biological Substance

As used herein, a labeled probe biological substance includes the above probe biological substance (such as an antibody and lectin) and the above label, and has a structure in which the above probe biological substance and the above label are bound via a suitable binding mode such as covalent bond, ionic bond, hydrogen bond, coordination bond, physical absorption and chemical absorption. From the viewpoint of binding strength, it may preferably have a structure in which they are bound via covalent bond such as amide bond, ester bond, imide bond, binding using thiol addition to a maleimide group, or biotin-avidin binding or biotin-streptavidin binding.

Such a labeled probe biological substance can be obtained by binding the above label to the above probe biological substance according to a standard method. Examples of specific labeling methods may include a method that uses an antibody (second antibody) having a specific affinity for the above probe biological substance, a biotin-avidin method, a thiol group-maleimide group coupling method, a method using a known chemical linker, a crosslinking method using a cross-linker (EDC etc.), an ionic binding method and the like. Among them, in the cases where the above probe biological substance is a humanized antibody or human antibody, preferable examples may include a coupling method of a thiol group-maleimide group with antibody or avidin.

A specific procedure for formation is, for example, as follows:

First, a first binding group is introduced into a probe biological substance, and a second binding group capable of binding to said first binding group is introduced into a label. A linker of a suitable chain length may be present in between the first binding group and the probe biological substance and between the second binding group and the label. The first and second binding groups may be chemical functional groups such as a carboxyl group, an amino group, an aldehyde group, a thiol group, and a maleimide group, and may be molecules such as biotin, avidin, and streptavidin. When a second antibody is used as the second binding group, the first binding group may be at a site other than the one that recognizes the "biological substance to be detected" constituting the probe biological substance.

As used herein, preferred examples of probe biological substances having the first binding group introduced therein, namely preferable examples of binding group-containing probe biological substances including the first binding group and the probe biological substance can include biotinylated probe biological substances such as a biotinylated antibody and a biotinylated lectin. On the other hand, preferred examples of labels having the second binding group introduced therein, namely preferable examples of binding group-containing labels including the second binding group and the label can include an avidin-bound label or a streptavidin-bound label. However, this does not exclude the use of an avidinated probe biological substance and a streptavidinated probe biological substance as the probe biological substance having the first binding group introduced therein, or the use of a biotinylated label as the label having the second binding group introduced therein. Nor does it exclude the use of those that adopted a chemical functional group instead of biotin or avidin (or streptavidin) as the first binding group in the probe biological substance having the first binding group introduced therein and as the second binding group in the label having the second binding group introduced therein.

Then, by reacting the probe biological substance having the first binding group introduced therein and the label having the second binding group introduced therein, a labeled probe biological substance can be obtained.

This labeled probe biological substance may be the one prepared in advance, in the absence of the tissue to be stained, by reacting a probe biological substance having the first binding group introduced therein and a label having the second binding group introduced therein, or the one prepared by reacting an unlabeled probe biological substance having the first binding group introduced therein to the tissue during the staining process followed by reacting the label having the second binding group introduced therein to the probe biological substance introduced into said tissue.

[Tissue Staining Method]

The tissue staining method of the present invention includes carrying out (A) a HE (hematoxylin-eosin) staining, and (B) a histochemical staining, serially on a single tissue section, wherein the histochemical staining is defined as a histochemical technique for detecting a biological substance to be detected in a tissue in a visible manner by use of a binding reaction between the biological substance to be detected and a probe biological substance capable of binding specifically to the biological substance to be detected (herein, such a histochemical staining is referred to as "histochemical staining (B)").

Thus, the tissue staining method of the present invention includes, serially, the steps of:

carrying out a HE staining, and carrying out a histochemical staining, on a single tissue section, wherein the histochemical staining is defined as a histochemical technique for detecting a biological substance to be detected in a tissue in a visible manner by use of a binding reaction between the biological substance to be detected and a probe biological substance capable of binding specifically to the biological substance to be detected.

According to the present invention, the "histochemical staining (B)" is not specifically limited as long as it is a histochemical technique for detecting a biological substance to be detected in a tissue in a visible manner by use of a binding reaction between the biological substance to be detected and a probe biological substance (i.e. a probe biological substance) capable of binding specifically to the biological substance to be detected. In the present invention, the "histochemical stainings (B)" may include immunohistochemical staining and lectin staining.

According to the present invention, either one of the HE staining (A) and the histochemical staining (B) may be carried out first. Nevertheless, in view of the fact that eosin, which is used in the HE staining, is water-soluble, it may be preferred that the histochemical staining (B) is carried out first followed by the HE staining since it can provide sufficient sensitivity of the HE staining and the histochemical staining (B). In this case, the tissue staining method of the present invention includes the steps of (1) carrying out a histochemical staining (B) on a tissue section (hereinafter referred to as the "histochemical staining step") and (3) carrying out a HE staining on said tissue section (hereinafter referred to as the "HE staining step").

The subject of the histochemical staining of the present invention is not limited to a pathological tissue section and can also be applied to cell staining.

(1) Histochemical Staining Step

According to the tissue staining method of the present invention, the histochemical staining step is a step of carrying out a histochemical staining (B) on a tissue section, i.e. a step of reacting a labeled probe biological substance obtained by introducing a label into a substance capable of recognizing a biological substance to be detected to a tissue section, to visualize the biological substance to be detected present on the tissue section via a specific binding reaction between the biological substances. According to the present invention, the histochemical staining (B), such as an immunohistochemical staining and a lectin staining, can be carried out using a conventionally known technique.

The method for preparing a section to which the tissue staining method of the present invention can be applied is not specifically limited, and any sections prepared by a known method can be used.

For example, when a paraffin-embedded section that is commonly used as a pathological section is used, the histochemical staining (B) may be carried out in the following procedure.

1) Deparaffinization Step

A pathological section is immersed in a vessel containing xylene to remove paraffin. The temperature may not be specifically limited and room temperature can be used. The immersion time may preferably be 3 minutes or more and 30 minutes or less. As needed, xylene may be replaced with a new one during the immersion step.

Then, the pathological section is immersed in a vessel containing ethanol to remove xylene. The temperature may not be specifically limited and room temperature can be used. The immersion time may preferably be 3 minutes or more and 30 minutes or less. As needed, ethanol may be replaced with a new one during the immersion step.

The pathological section is immersed in a vessel containing water to remove ethanol. The temperature may not be specifically limited and room temperature can be used. The immersion time may preferably be 3 minutes or more and 30 minutes or less. As needed, water may be replaced with a new one during the immersion step.

2) Activation Step

When a histochemical staining (B) and an immunohistochemical staining are carried out, the biological substance of interest is subjected to activation treatment according to a known method. The activation condition is not specifically defined, and as an activation solution, 0.01 M citrate buffer (pH 6.0), 1 mM EDTA solution (pH 8.0), 5% urea, 0.1 M Tris-HCl buffer etc. may be used. As a heating apparatus, there can be used an autoclave, a microwave oven, a pressure cooker, a waterbath etc. The temperature is not specifically limited, but may be room temperature. The temperature may be 50 to 130° C. and the time may be 5 to 30 minutes.

Subsequently, to a vessel containing PBS, the activated section is immersed for washing. The temperature is not specifically limited, but may be room temperature. The immersion time may preferably be 3 minutes or more and 30 minutes or less. As needed, PBS may be replaced with a new one during the immersion step.

3) Staining Step with a Labeled Probe Biological Substance

A PBS dispersion of the above labeled probe biological substance is prepared, and is placed on the pathological section to allow it to react to the biological substance to be detected. For example, when an immunohistochemical staining is carried out as the histochemical staining (B), a PBS dispersion of the labeled antibody is prepared, and is placed on the pathological section to allow it to react to the biological substance to be detected. Also, when a lectin staining is carried out as the histochemical staining (B), a PBS dispersion of the labeled lectin is prepared, and is placed on the pathological section to allow it to react to the biological substance to be detected.

As used herein, when a plurality of "biological substances to be detected" are to be stained, a PBS dispersion of a fluorescent body having a "probe biological substance" corresponding to the "biological substance to be detected" and a fluorescent substance is prepared for each "probe biological substance", wherein each of the fluorescent substances is different from each other, and the PBS dispersions are placed on the pathological section to allow them to react to the biological substances to be detected. When being placed on the pathological section, the PBS dispersion of each fluorescent body may be mixed in advance or may be placed sequentially.

The temperature is not specifically limited and may be room temperature. The reaction time may preferably be 30 minutes or more and 24 hours or less. Prior to staining with a fluorescent body, a known blocking agent such as a BSA-containing PBS may preferably be added dropwise.

Subsequently, to a vessel containing PBS, the stained section is immersed to remove the unreacted fluorescent body. The temperature is not specifically limited and may be room temperature. The immersion time may preferably be 3 minutes or more and 30 minutes or less. As needed, PBS may be replaced with a new one during the immersion step.

(2) Fixation Treatment Step

The fixation treatment step carried out as needed in the tissue staining method of the present invention is a step of fixing a labeled probe biological substance introduced by the above immunohistochemical staining step on a tissue section.

According to the tissue staining method of the present invention, when (1) Histochemical staining step described above is followed by (3) HE staining step described below, the stained tissue section obtained by the histochemical staining step may be directly subjected to the HE staining step. However, after the histochemical staining, a fixation step may preferably be carried out prior to the HE staining, since it permits inhibition of reduction in light-emission intensity from the fluorescent body introduced into the tissue section as a label after the HE staining step.

Fixation solutions for use in the present invention include cross-linking agents such as formalin, paraformaldehyde, glutaraldehyde, acetone, ethanol, and methanol, and cell membrane permeable substances.

As used herein, the fixation process can be carried out using a conventionally known technique. Specifically, the fixation process may be carried out by immersing a stained tissue section obtained by the histochemical staining step in such a fixation solution. For example, a stained tissue section obtained in the histochemical staining step is immersed in an aqueous solution of dilute paraformaldehyde for about several minutes to several hours.

(3) HE Staining Step

According to the tissue staining method of the present invention, the HE staining step is a step of staining a tissue section using hematoxylin and eosin in order to obtain information on the morphology of the tissue section. According to the present invention, the HE staining (A) may be carried out by a conventionally known technique.

Hematoxylin is a blue violet dye, and stains cell nuclei, bone tissues, some cartilage tissues, serous components (basophilic tissues etc.) and the like. Eosin is a red-pink dye and stains cytoplasm, the connective tissue of the soft tissue, red blood cells, fibrin, endocrine granules (eosinophilic tissues etc.) and the like. Among them, eosin emits autofluorescence. Thus, according to the present invention in which a HE staining is carried out in conjunction with an immunohistochemical staining, when an excitation light is applied, the autofluorescence emitted by eosin that stained cytoplasm etc. together with the autofluorescence emitted by the tissues etc. makes it easier to obtain information on the morphology of the cells or tissue.

According to the present invention, (3) HE staining step may be carried out before the above (1) Histochemical staining step or after (1) Histochemical staining step. As used herein, when (3) HE staining step is carried out before (1) the histochemical staining step, "1) Deparaffinization step" and "2) Activation step" described in "(1) Histochemical staining step" are carried out before the HE staining.

However, considering that eosin is a water soluble substance, (3) HE staining step may preferably be carried out after (1) Histochemical staining step. Because, in such a case, the introduction of a label by the histochemical staining (B) can be adequately carried out and the HE staining (A) can also be adequately carried out. On the other hand, when (1) Histochemical staining step is carried out after (3) HE staining step, eosin that was introduced into the tissue section by the HE staining (A) can elute into the PBS dispersion of the labeled probe biological substance during the above "3) Staining step with a labeled probe biological substance" in (1) Histochemical staining step, which can reduce the sensitivity of the HE staining (A) and can make the histochemical staining (B) insufficient.

After a series of staining processes by (1) Histochemical staining step and (3) HE staining step, a cover glass is placed on the section to encapsulate it. In order to facilitate (4) Observation step described below, encapsulation with the cover glass may be preceded by the dehydration of the stained tissue section as well as clarification in order to increase the clarity of the tissue section. As used herein, dehydration may be carried out by immersing the stained tissue section in ethanol etc., and clarification may be carried out by immersing the dehydrated stained tissue section in xylene followed by air-drying.

(4) Observation Step

According to the present invention, an observation step may be carried out after the above steps (1) to (3).

The observation step is a step of irradiating the tissue section stained in the above steps with an excitation light, to give the morphological information of the cell or tissue (cell morphology information) based on the autofluorescence of the tissue or the autofluorescence of eosin, and to give information on the distribution of the above "biological substance to be detected" in the cell or tissue based on fluorescent images with the above label (hereinafter referred to as "biological molecule distribution information"). The "biological molecule distribution information" is obtained as information on the distribution of specific antigen molecule in the cell or tissue when immunohistochemical staining was carried out as the histochemical staining (B), and, when lectin staining was carried out as the histochemical staining (B), as information on the distribution of a specific sugar chain or a modified molecule or a complex thereof in the cell or tissue.

The excitation light may be any light, as long as it has an appropriate wavelength so as to allow the tissue section and eosin used as needed to emit autofluorescence, and to allow a fluorescent substance constituting the label to emit fluorescence of the desired wavelength, and the means for applying the excitation light is not specifically limited. For example, a tissue section may be irradiated with an excitation light having an appropriate wavelength and output, the excitation light being provided from a laser beam source provided in a fluorescent microscope using a filter that selectively transmits a given wavelength as needed.

Information on cell morphology and information on biological molecule distribution may preferably be obtained in a single view field, in other words, obtained based on each of autofluorescence of the tissue section and fluorescence emitted from the label, both of which are obtained from a single stained section, and are distinguished and recognized while allowed in a single view field. When desired, needless to say, by using a suitable filter that can adequately reduce only one of autofluorescence of the tissue section and fluorescence emitted from the label, information on cell morphology may only be obtained in a view field, and information on biological molecule distribution may be obtained in another view field.

While the excitation light in the observation step is not specifically limited as long as fluorescence emitted from the label with respect to autofluorescence of the tissue section and light emission derived from HE staining can be recognized, those lights are preferable which have a peak in the range outside of 400 nm or greater and less than 560 nm, specifically in the range of 400 nm or less and in the range of 560-630 nm, from the viewpoint of preventing excessive intensity of autofluorescence from the tissue section and light emission from HE staining. Considering that biological substances that can be easily decomposed by short-wavelength ultraviolet irradiation, such as nucleic acids, can be a biological substance to be detected, those lights may be preferred which have a peak in the range of 350 nm or greater and 400 nm or less or in the range of 560-630 nm.

As fluorescent substances constituting a fluorescent body used as the above label, there can preferably be used those substances that emit fluorescence, by the above excitation light, having a peak in the range of 580 nm or greater, preferably in the range of 580-690 nm, more preferably in the range of 600-630 nm (thus, fluorescence having an emission wavelength in this range is measured).

Furthermore, information on cell morphology and information on biological molecule distribution may be obtained from a (fluorescent) microscope tube so as to permit quick observation or may be obtained by displaying an image taken by a camera installed in a (fluorescent) microscope on a separate display means (a monitor etc.) and observing it. Even if sufficient information on biological molecule distribution cannot be obtained visually from the microscope tube, there may be cases in which information on biological molecule distribution can be obtained from an image taken by a camera though this depends on the fluorescent substance constituting the fluorescent body used as a label.

Examples of acquisition of the above information on biological molecule distribution include measurement of the number of molecules of the "biological substance to be detected" or the density of the "biological substance to be detected" (i.e. the number of molecules of the "biological substance to be detected" per unit area) per cell. There can be selected an excitation light source and an optical filter for fluorescence detection corresponding to the absorption maximum wavelength and fluorescence wavelength of a fluorescent substance constituting the fluorescent body used as a label. For determination of bright points or emission brightness, a commercially available image analysis software (for example, an automated bright spots measuring software G-Count by G-Angstrom) may preferably be used, but the measuring method is not specifically limited.

EXAMPLES

Example 1: Preparation of a Label

<Biotinylated Trastuzumab>

As trastuzumab, Herceptin (registered trademark) in powder form manufactured by Roche in the form of a pharmaceutical drug was used, and this was biotinylated by use of Biotin Labeling kit-SH (Doujin), to give biotinylated trastuzumab.

<Streptavidin-Modified HRP>

As streptavidin-modified HRP, High Sensitivity Streptavidin-HRP (Thermo Scientific) was used.

Streptavidin-Modified Fluorescent Aggregate

Synthesis of a Fluorescent Aggregate

Synthetic Example 1 (Synthesis of an Organic Fluorescent Dye (Tetramethyl Rhodamine)-Aggregated Silica Nanoparticles)

6.6 mg of tetramethyl rhodamine (Invitrogen TAMRA-SE) (excitation wavelength 550 nm, emission wavelength 570 nm) and 3 μl of 3-aminopropyl trimethoxysilane (manufactured by Shin-Etsu Silicone Co., Ltd., KBM903) were mixed in DMF to give an organo alkoxysilane compound. 0.6 ml of the organo alkoxysilane compound obtained was mixed with 48 ml of ethanol, 0.6 ml of TEOS (tetraethoxysilane), 2 ml of water, and 2 ml of aqueous 28% ammonia for 3 hours.

The mixture prepared in the above step was centrifuged at 10,000 g for 20 minutes, and the supernatant was discarded. Ethanol was added to disperse the precipitate, which was centrifuged again. In a similar procedure, washing with ethanol and pure water was each carried out twice. As a result, 10 mg of tetramethyl rhodamine-aggregated silica nanoparticles were obtained as a fluorescent aggregate.

One thousand particles of the tetramethyl rhodamine-aggregated silica nanoparticles were subjected to SEM observation, and the average particle size of 104 nm was obtained with its coefficient of variation of 12%.

Synthetic Example 2 (Synthesis of Organic Fluorescent Dye (Texas Red)-Aggregated Silica Nanoparticles)

Except that tetramethyl rhodamine was replaced with Texas Red (TXR-SE manufactured by Invitrogen) (excitation wavelength 590 nm, emission wavelength 610 nm) as an organic fluorescent dye, a method similar to the above Synthetic example 1 was followed to give Texas Red-aggregated silica nanoparticles. One thousand particles of the Texas Red-aggregated silica nanoparticles were subjected to SEM observation, and the average particle size of 109 nm was obtained with its coefficient of variation of 11%.

Synthetic Example 3 (Synthesis of Organic Fluorescent Dye (Cy5)-Aggregated Silica Nanoparticles)

Except that tetramethyl rhodamine was replaced with Cy5 as an organic fluorescent dye, a method similar to the above Synthetic example 1 was followed to give Cy5-aggregated silica nanoparticles. One thousand particles of the Cy5-aggregated silica nanoparticles were subjected to SEM observation, and the average particle size of 98 nm was obtained with its coefficient of variation of 13%.

Synthetic Example 4 (Synthesis of Organic Fluorescent Dye (FITC)-Aggregated Silica Nanoparticles)

Except that tetramethyl rhodamine was replaced with FITC as an organic fluorescent dye, a method similar to the above Synthetic example 1 was followed to give FITC-aggregated silica nanoparticles. One thousand particles of the FITC-aggregated silica nanoparticles were subjected to SEM observation, and the average particle size of 102 nm was obtained with its coefficient of variation of 14%.

Synthetic Example 5 (Synthesis of Semiconductor Nanoparticles (Qdot565)-Aggregated Silica Nanoparticles)

To 10 μl of CdSe/ZnS decane dispersion (Qdot565 manufactured by Invitrogen), 0.1 mg of TEOS, 0.01 ml of ethanol, and 0.03 ml of aqueous concentrated ammonia were added, which were then hydrolyzed by stirring for 3 hours.

The mixture prepared in the above step was centrifuged at 10,000 g for 20 minutes, and the supernatant was discarded. Ethanol was added to disperse the precipitate, which was centrifuged again. In a similar procedure, washing with ethanol and pure water was each carried out twice. As a result, as a fluorescent aggregate, 60 mg of Qdot565-aggregated silica nanoparticles were obtained.

One thousand particles of the Qdot565-aggregated silica nanoparticles were subjected to SEM observation, and the average particle size of 108 nm was obtained with its coefficient of variation of 14%.

Synthetic Example 6 (Synthesis of Semiconductor Nanoparticles (Qdot625)-Aggregated Silica Nanoparticles)

Except that Invitrogen's Qdot565 was replaced with Invitrogen's Qdot625 as semiconductor nanoparticles, a method similar to the above Synthetic example 5 was followed to give Qdot625-aggregated silica nanoparticles.

One thousand particles of the Qdot625-aggregated silica nanoparticles were subjected to SEM observation, and the average particle size of 102 nm was obtained with its coefficient of variation of 13%.

Binding of Streptavidin to a Fluorescent Aggregate

The binding of streptavidin to each of the above fluorescent aggregates was carried out according to the following procedure to give each of the corresponding streptavidin-bound fluorescent aggregates.

To PBS (phosphate buffered saline) containing 2 mM EDTA (ethylenediaminetetraacetic acid), a fluorescent aggregate was dissolved to 3 nM. To this solution, SM(PEG) 12 (manufactured by Thermo Scientific, succinimidyl-[(N-maleomidopropionamid)-dodecaethyleneglycol]ester) was mixed to a final concentration of 10 mM and reacted for 1 hour. This mixture was centrifuged at 10,000 g for 20 minutes, and the supernatant was discarded. Then PBS containing 2 mM EDTA was added to disperse the precipitate, which was centrifuged again. In a similar procedure, washing was carried out three times to give a fluorescent aggregate for antibody binding.

On the other hand, streptavidin was subjected to a reduction treatment with 1 M dithiothreitol (DTT) or a the addition of thiol group such as SATA, and an excess of the reaction reagent was removed by use of a gel filtration column to give a reduced antibody solution capable of binding to silica particles.

The fluorescent aggregate for antibody binding and the reduced antibody obtained as above were mixed in PBS containing 2 mM EDTA, and reacted for 1 hour. 10 mM mercaptoethanol was added to stop the reaction. The solution obtained was centrifuged at 10,000 g for 20 minutes, and the supernatant was discarded. Then PBS containing 2 mM EDTA was added to disperse the precipitate, which was centrifuged again. In a similar procedure, washing was carried out three times to give a streptavidin-bound fluorescent aggregate.

By the above procedure, from tetramethyl rhodamine-aggregated silica nanoparticles, Texas Red-aggregated silica nanoparticles, Cy5-aggregated silica nanoparticles, FITC-aggregated silica nanoparticles, Qdot565-aggregated silica nanoparticles, and Qdot625-aggregated silica nanoparticles, streptavidin-bound tetramethyl rhodamine-aggregated silica nanoparticles, streptavidin-bound Texas Red-aggregated silica nanoparticles, streptavidin-bound Cy5-aggregated silica nanoparticles, streptavidin-bound FITC-aggregated silica nanoparticles, streptavidin-bound Qdot565-aggregated silica nanoparticles, and streptavidin-bound Qdot625-aggregated silica nanoparticles, respectively, were each obtained as a streptavidin-bound fluorescent aggregate.

Example 2: Effect by the Presence or Absence of Fixation Treatment

In relation to immunohistochemical staining and HE staining on a single tissue section, the effect of the presence or absence of fixation treatment in between the immunohistochemical staining and HE staining was evaluated in the following method.

(1) Immunohistochemical Staining

Using biotinylated trastuzumab prepared in Example 1 and Cy5-labeled streptavidin (Invitrogen), the immunohistochemical staining of a human breast tissue was carried out in the following procedure. As a section for staining, a tissue array slide (CB-A712) of Cosmo Bio for which the FISH score has been calculated beforehand using the PathVysion HER-2 DNA Probe Kit (Abbott) was used.

After the tissue array slide was deparaffinized, the solvent was replaced and the slide was washed with water. The resultant tissue array slide was then subjected to autoclaving in 10 mM citrate buffer (pH 6.0) for 15 minutes to activate the antigen. The tissue array slide after the activation of the antigen was washed with a PBS buffer, and then was subjected to blocking using 1% BSA-containing PBS buffer in a wet chamber for 1 hour. After blocking, biotinylated trastuzumab diluted to 0.05 nM in 1% BSA-containing PBS buffer was reacted with the tissue section for 2 hours, and then washed. Furthermore, it was reacted with Cy5-labeled streptavidin for 0.5 hour, and after washing, an immunohistochemically stained section was obtained.

(2) Fixation Treatment

The immunohistochemically stained section obtained in the above (1) was subjected to fixation treatment by immersing it in an aqueous 4% neutral paraformaldehyde-based buffer solution for 10 minutes.

(3) HE Staining

The immunohistochemically stained section that was fixation-treated in the above (2) was subjected to HE staining. The stained section was immersed in ethanol to dehydrate, and the resultant dehydrated section was further immersed in xylene and air-dried to carry out clarification to give a double-stained section.

(4) Observation

The double-stained section obtained in the above (3) was encapsulated in a slide glass, and was examined under microscope using Olympus's BX53.

In order to confirm the effects of the double-stained section obtained after undergoing the above (1) to (3) (hereinafter referred to as "double-stained sample with fixation treatment"), a double-stained section obtained in a method similar to the "double-stained sample with fixation treatment" except that it was not subjected to the above (2) (hereinafter referred to as "double-stained sample without fixation treatment) and a stained section obtained by carrying out only the above (1) (hereinafter referred to as "non-HE stained sample") were observed in a method similar to the above (4), respectively, as control experiments.

As a result of observation and comparison, by carrying out the fixation treatment, HE staining can be carried out while maintaining the staining property of immunohistochemical staining (Table 3).

TABLE 3

Observation Result

| Sample | Fixation treatment | Observation result |
|---|---|---|
| Double-stained sample with fixation treatment | Yes | Light emission derived from Cy5 comparable to non-HE stained sample was observed in the cell membrane. |
| Double-stained sample without fixation treatment | No | Light emission derived from Cy5 weaker than non-HE stained sample was observed in the cell membrane. |

Example 3: Effect of Light Emission Wavelength of a Fluorescent Body

In relation to immunohistochemical staining and HE staining on a single tissue section, the effect of the wavelength characteristics of fluorescence emitted from a fluorescent body used as a label for immunohistochemical staining was evaluated in the following method.

Using, as a label for immunohistochemical staining, each of Cy5-labeled streptavidin, Texas Red-labeled streptavidin, tetramethyl rhodamine (TAMRA)-labeled streptavidin, FITC-labeled streptavidin, Qdot565-labeled streptavidin, and Qdot625-labeled streptavidin in a procedure similar to the above steps (1) to (3) in Example 2, immunohistochemical staining, fixation treatment, HE staining, dehydration and clarification were carried out to give double-stained sections.

Each of the double-stained sections was examined under microscope using Olympus's BX53.

As shown in the following Table 4, in the double-stained sections in which Cy5, Texas Red and Qdot625 were used as a label for immunohistochemical staining, it was possible to observe fluorescence emission from the label without being buried in autofluorescence of the tissue.

TABLE 4

| Label | Excitation wavelength of the label | Emission wavelength of the label | Observation result |
|---|---|---|---|
| Cy5 | 630 nm | 690 nm | Light emission was observed in cell membrane. |

TABLE 4-continued

| Label | Excitation wavelength of the label | Emission wavelength of the label | Observation result |
|---|---|---|---|
| Texas Red | 590 nm | 610 nm | Light emission was observed in cell membrane. |
| TAMRA | 550 nm | 570 nm | Light emission from the entire tissue. |
| FITC | 480 nm | 520 nm | Light emission from the entire tissue. |
| Qdot565 | 365 nm | 565 nm | Light emission from the entire tissue. |
| Qdot625 | 365 nm | 625 nm | Light emission was observed in cell membrane. |

Example 4: Effect of the Type of the Fluorescent Body in Microscopic Observation Using, as a label for immunohistochemical staining, each of Cy5-labeled streptavidin, Texas Red-labeled streptavidin, Qdot625-labeled streptavidin, Texas Red-aggregated/silica nanoparticle-labeled streptavidin, Cy5-aggregated/silica nanoparticle-labeled streptavidin and Qdot625-aggregated/silica nanoparticle-labeled streptavidin, respectively, was used and, in a procedure similar to the above steps (1) to (3) in Example 2, immunohistochemical staining, fixation treatment, HE staining, dehydration and clarification were carried out to give double-stained sections.

Each of the double-stained sections was examined under microscope. For observation, Olympus's BX53 was used as a common fluorescent microscope, and FV1000-D was used as a confocal laser microscope.

As a result of observation, as shown in the following Table 5, when fluorescent body-aggregated silica nanoparticles are used as a fluorescent body, it was found, bright spots can be observed using a common microscope. Also, while the Cy5-aggregated silica nanoparticles cannot be visually observed, it was revealed, light emission from the Texas Red-aggregated silica nanoparticles and Qdot625-aggregated silica nanoparticles can be visually confirmed.

On the other hand, in the case of the double-stained sections immunohistochemically stained with Qdot625 that is not in the form of fluorescent body-aggregated silica nanoparticles, bright spots were observed with a confocal laser microscope. However, with a common fluorescent microscope, bright spots were observed as a light emission region in a plane form formed by connected bright spots due to the fineness of bright spots, and respective bright spots could not be individually and separately recognized.

TABLE 5

| | Microscope BX53 | | | Microscope FV1000-D | | |
|---|---|---|---|---|---|---|
| Label | Observation of light emission (visual) | Observation of light emission (monitor) | Observation of bright spots | Observation of light emission (visual) | Observation of light emission (monitor) | Observation of bright spots |
| Cy5 | X | ○ | X | X | ○ | X |
| Texas Red | ○ | ○ | X | ○ | ○ | X |
| Qdot625 | ○ | ○ | X | ○ | ○ | ○ |
| Cy5-aggregated silica nanoparticles | X | ○ | ○ | X | ○ | ○ |
| Texas Red-aggregated silica nanoparticles | ○ | ○ | ○ | ○ | ○ | ○ |
| Qdot625-aggregated silica nanoparticles | ○ | ○ | ○ | ○ | ○ | ○ |

Example 5: Measurement of Bright Spots

Using the sections stained with the Texas Red-aggregated silica nanoparticles prepared in Example 4, images were obtained, cancer cell regions were identified, binary processing using the image J was carried out, and after noise canceling, bright spots were measured to determine the number of bright spots per 10 cells. Measurement of bright spots was performed on 20 spots on the slide.

Table 6 shows a comparison of scores of bright spots stained with the Texas Red-aggregated silica nanoparticles and the FISH scores. Table 7 shows a correlation comparison of scores of bright spots stained with the Texas Red-aggregated silica nanoparticles and the FISH scores. The scores calculated this time exhibit a high correlation with the FISH scores, suggesting the usefulness as a diagnostic method as well.

TABLE 6

Number of Bright Spots and FISH Scores

| | Bright spot score per 10 cells | FISH score |
|---|---|---|
| Spot 1 | 46.33 | 1.02 |
| Spot 2 | 11.98 | 1.14 |
| Spot 3 | 10.62 | 1.18 |
| Spot 4 | 18.36 | 1.32 |
| Spot 5 | 29.66 | 1.44 |
| Spot 6 | 10.69 | 1.03 |
| Spot 7 | 48.31 | 1.22 |

TABLE 6-continued

Number of Bright Spots and FISH Scores

| | Bright spot score per 10 cells | FISH score |
|---|---|---|
| Spot 8 | 104.83 | 1.19 |
| Spot 9 | 110.34 | 1.69 |
| Spot 10 | 192.66 | 1.88 |
| Spot 11 | 386.89 | 2.44 |
| Spot 12 | 369.28 | 2.88 |
| Spot 13 | 491.92 | 3.86 |
| Spot 14 | 616.38 | 4.22 |
| Spot 15 | 557.02 | 4.63 |
| Spot 16 | 669.46 | 6.49 |
| Spot 17 | 750.02 | 6.36 |
| Spot 18 | 886.19 | 8.01 |
| Spot 19 | 994.93 | 8.13 |
| Spot 20 | 806.31 | 8.66 |

TABLE 7

Correlation Comparison with the FISH Method

| | Texas Red-aggregated silica nanoparticles |
|---|---|
| Correlation coefficient | 0.967324009 |

Example 6: Effect of the Presence or Absence of Fixation Treatment in Lectin Staining In relation to lectin staining and HE staining on a single tissue section, the effect of the presence or absence of the fixation treatment in between the lectin staining and the HE staining was evaluated in the following method.

(1) Lectin Staining

Using J-OIL MILLS's biotinylated ConA (Cat. No. 300410) and the streptavidin-bound Texas Red-aggregated silica nanoparticles synthesized in Example 1, a human breast tissue was lectin stained in the following procedure.

After deparaffinizing a tissue array slide, the solvent was replaced and the slide was washed with water. The resultant slide was then subjected to blocking in PBS buffer containing 0.05% Tween 20 and 1% BSA in a wet chamber for 1 hour. After blocking, biotinylated ConA diluted to 0.05 nM in 1% BSA-containing PBS buffer was reacted with the tissue section for 1 hour, and then the resultant tissue section was washed. Furthermore, it was reacted with streptavidin-bound Texas Red-aggregated silica nanoparticles for 0.5 hour, and after washing, an immunohistochemically stained section was obtained.

(2) Fixation Treatment

The immunohistochemically stained section obtained in the above (1) was subjected to fixation treatment by immersing it in an aqueous 4% neutral paraformaldehyde-based buffer solution for 10 minutes.

(3) HE Staining

The immunohistochemically stained section obtained by the fixation treatment in the above (2) was subjected to HE staining. The stained section was immersed in ethanol to dehydrate, and the dehydrated section was further immersed in xylene and air-dried to carry out clarification to give a double-stained section.

(4) Observation

The double-stained section obtained in the above (3) was encapsulated in a slide glass, and was examined under microscope using Olympus's BX53.

In order to confirm the effects of the double-stained section obtained after undergoing the above (1) to (3) (hereinafter referred to as "double-stained sample with fixation treatment"), a double-stained section obtained in a method similar to the "double-stained sample with fixation treatment" except that it was not subjected to the above (2) (hereinafter referred to as "double-stained sample without fixation treatment") and a stained section obtained by carrying out only the above (1) (hereinafter referred to as "non-HE stained sample") were observed in a method similar to the above (4), respectively, as control experiments.

As a result of observation and comparison, by carrying out the fixation treatment, it was found that HE staining can be carried out while maintaining the staining property of immunohistochemical staining (Table 8).

TABLE 8

Observation Result

| Sample | Fixation treatment | Observation result |
|---|---|---|
| Double-stained sample with fixation treatment | Yes | Light emission derived from Texas Red comparable to non-HE stained sample was observed in the cytoplasm. |
| Double-stained sample without fixation treatment | No | Light emission derived from Texas Red weaker than non-HE stained sample was observed in the cytoplasm. |

The invention claimed is:

1. A tissue staining method comprising:
providing a tissue section for histochemical staining, wherein the tissue section comprises a target substance and the tissue section is embedded in paraffin;
removing the paraffin from the tissue section;
reacting a labeled probe with the target substance in the tissue to obtain a histochemical stained tissue section;
fixing the histochemical stained tissue section to create a fixed histochemical stained tissue section;
staining the fixed histochemical stained tissue section with a hematoxylin and eosin (HE) stain to obtain a HE stained, histochemical stained tissue section;
irradiating the HE stained, histochemical stained tissue section with an excitation light;
obtaining a morphological image of the irradiate, HE stained, histochemical stained tissue section by imaging the irradiate, HE stained, histochemical stained tissue with a camera and obtaining a fluorescent image of the tissue or a fluorescent image of the eosin;
determining a distribution of the target substance to be detected from the irradiate, HE stained, histochemical stained tissue section by obtaining a fluorescent image of the labeled probe with a camera,
wherein the labeled probe specifically binds to the target substance to be detected in the tissue section and provides the fluorescent signal showing the distribution of the target substance,
wherein the labeled probe comprise a probe and a label,
wherein the label is a fluorescent aggregate comprising a particle having a plurality of organic fluorescent dyes on the surface of or inside the particle and has an emission wavelength of 580 nanometer (nm) or greater,
wherein the fluorescent aggregate has an excitation wavelength of 580 nm or greater,
wherein the fluorescent aggregate has an excitation wavelength ranging from 560 nm to 590 nm, and wherein the fluorescent aggregate has an average particle size ranging from 50 nm to 200 nm.

2. The tissue staining method according to claim 1, wherein the histochemical staining is immunohistochemical staining.

3. The tissue staining method according to claim 1, wherein the histochemical staining is lectin staining.

4. The tissue staining method according to claim 1, wherein the fluorescent aggregate is
- a core/shell-structure particle having a core and the organic fluorescent dyes immobilized on the core, or
- a fluorescent body-encapsulating nanoparticle having a substrate and the organic fluorescent dyes encapsulated in the substrate.

5. The tissue staining method according to claim 1, wherein the particle of the fluorescent aggregate is a silica nanoparticle.

6. The tissue staining method according to claim 1, wherein a variation coefficient of diameter of the fluorescent aggregate is not more than 15%.

7. The tissue staining method according to claim 1, wherein a variation coefficient of diameter of the fluorescent aggregate is in a range of 5 to 15%.

\* \* \* \* \*